US007279508B2

(12) United States Patent
Bellare et al.

(10) Patent No.: US 7,279,508 B2
(45) Date of Patent: *Oct. 9, 2007

(54) NANOCOMPOSITE SURGICAL MATERIALS AND METHOD OF PRODUCING THEM

(75) Inventors: Anuj Bellare, Brighton, MA (US); Wolfgang Fitz, South Natick, MA (US); Andreas H. Gomoll, Brookline, MA (US); Richard D. Scott, Dedham, MA (US); Thomas S. Thornhill, Dover, MA (US)

(73) Assignee: The Brigham and Women's Hospital, Inc., Boston, MA (US)

(*) Notice: Subject to any disclaimer, the term of this patent is extended or adjusted under 35 U.S.C. 154(b) by 491 days.

This patent is subject to a terminal disclaimer.

(21) Appl. No.: 10/734,652

(22) Filed: Dec. 12, 2003

(65) Prior Publication Data

US 2004/0180986 A1    Sep. 16, 2004

Related U.S. Application Data

(63) Continuation of application No. 09/541,374, filed on Mar. 31, 2000, now Pat. No. 6,689,823.

(60) Provisional application No. 60/127,244, filed on Mar. 31, 1999.

(51) Int. Cl.
  *A61F 2/00* (2006.01)
  *C08K 9/04* (2006.01)
  *A61K 6/08* (2006.01)

(52) U.S. Cl. .................. 523/117; 523/210; 977/DIG. 1

(58) Field of Classification Search ................ 523/117, 523/210
See application file for complete search history.

(56) References Cited

U.S. PATENT DOCUMENTS

| | | | |
|---|---|---|---|
| 3,156,666 A | 11/1964 | Pruett | |
| 3,471,439 A | 10/1969 | Bixler et al. | |
| 4,124,562 A | 11/1978 | Yui et al. | |
| 4,239,113 A | 12/1980 | Gross et al. | |
| 4,373,217 A | 2/1983 | Draenert | |
| 4,396,476 A | 8/1983 | Roemer et al. | |
| 4,473,665 A | 9/1984 | Martini-Vvedensky et al. | |
| 4,490,497 A | 12/1984 | Evrard et al. | |
| 4,500,658 A | 2/1985 | Fox | |
| 4,588,583 A | 5/1986 | Pietsch et al. | |
| 4,617,327 A | 10/1986 | Podsun | |
| 4,735,625 A | 4/1988 | Davidson | |
| 4,791,150 A | 12/1988 | Braden et al. | |
| 5,030,474 A | 7/1991 | Saita et al. | |
| 5,055,497 A | 10/1991 | Okada et al. | |
| 5,328,262 A | 7/1994 | Lidgren et al. | |
| 5,334,356 A | 8/1994 | Baldwin et al. | |
| 5,574,075 A | 11/1996 | Draenert | |
| 5,795,922 A | 8/1998 | Demian et al. | |
| 5,797,873 A | 8/1998 | Franz et al. | |
| 5,847,046 A | 12/1998 | Jiang et al. | |
| 6,013,591 A | 1/2000 | Ying et al. | |
| 6,020,396 A | 2/2000 | Jacobs | |
| 6,080,801 A | 6/2000 | Draenert et al. | |
| 6,143,211 A * | 11/2000 | Mathiowitz et al. ........... 264/4 |
| 6,197,410 B1 | 3/2001 | Vallittu et al. | |
| 6,203,844 B1 | 3/2001 | Park | |
| 6,689,823 B1 * | 2/2004 | Bellare et al. .............. 523/115 |
| 2004/0029996 A1 | 2/2004 | Kuhn | |

FOREIGN PATENT DOCUMENTS

| | | |
|---|---|---|
| DE | 42 29 947 A1 | 8/1992 |
| EP | 0 041 614 A1 | 12/1981 |
| EP | 0 089 782 A1 | 9/1983 |
| EP | 0 768 067 A2 | 4/1997 |
| EP | 0 796 653 A2 | 9/1997 |
| EP | 0 853 929 A2 | 7/1998 |
| EP | 0 872 223 A1 | 10/1998 |
| EP | 0 875 456 A1 | 11/1998 |
| EP | 1 095 984 A1 | 5/2001 |
| EP | 1 293 531 A1 | 3/2003 |
| EP | 1 366 774 A1 | 4/2003 |
| GB | 1 278 413 | 6/1972 |
| GB | 1 532 318 | 11/1976 |
| WO | WO93/25245 | 12/1993 |
| WO | WO96/07472 A1 | 3/1996 |
| WO | WO96/11714 | 4/1996 |

(Continued)

OTHER PUBLICATIONS

Souheng Wu, E., "A Generalized Criterion for Rubber Toughening: The Critical Matrix Ligament Thickness," *J. Appl. Polymer Sci.*, 35: 549-561 (1988).

(Continued)

*Primary Examiner*—Tae H Yoon
(74) *Attorney, Agent, or Firm*—Hamilton, Brook, Smith & Reynolds, P.C.

(57) ABSTRACT

Nanocomposite surgical materials, such as cements, having very fine heterogenous structure are formed by incorporating into a polymeric matrix a well dispersed solid filler having an average mass diameter ranging from about 750 nanometers to about 1 nanometer. The average ligament thickness of the surgical composite cements ranges from about 750 nanometers to about 1 nanometer. Methods and apparatus for avoiding air contact during the preparation and transfer of a cement to an in vivo site are described.

20 Claims, 7 Drawing Sheets

FOREIGN PATENT DOCUMENTS

| WO | WO96/40424 | 12/1996 |
|---|---|---|
| WO | WO97/18031 | 5/1997 |
| WO | WO97/21485 | 6/1997 |

OTHER PUBLICATIONS

Lewis, G., "Properties of Acrylic Bone Cement: State of the Art Review," *J. Biomed. Mater. Res.*, 38(2): 155-182 (1997).
Molino, L. N., and Topoleski, L.D.T., "Effect of $BaSO_4$ on the Fatigue Crack Propagation Rate of PMMA Bone Cement," *J. Biomed. Mater. Res.*, 31: 131-137 (1996).
Jacoby, M., "Photonic Crystals: Whole Lotta Holes Prepared by New Procedures, Materials With Arrays of Large Holes May Hasten Development of Optical-based Technologies," *C&EN*, 11-23 38-43 (1998).
Lewis, G., "Research Directions in Acrylic Bone Cement Studies," *BMES Bul.*, 20(1): 4-20 (1996).
Wang, J. S., et al., "Porosity of Bone Cement Reduced by Mixing and Collecting Under Vacuum," *Acta Orthop. Scand.*, 64(2): 143-146 (1993).
Wixson, R., et al., "Vacuum Mixing Acrylic Bone Cement," *J. Arthroplasty*, 2(2): 141-149 (1987).
Saha, S. and Pal, S., "Mechanical Properties of Bone Cement: A Review," *J. Biomed. Mater. Res.*, 18: 435-462 (1984).
Pascual, B., et al., "New Aspects of the Effect of Size and Size Distribution on the Setting Parameters and Mechanical Properties of Acrylic Bone Cements," *Biomaterials*, 17(5): 509-516 (1996).
James, S. P., et al., "Extensive Porosity at the Cement-Femoral Prosthesis Interface: A Preliminary Study," *J. Biomed. Mater. Res.*, 27: 71-78 (1993).
Fumich, R.M. and Gibbons, D. F., "Rate of Mixing and the Strength of Methylmethacrylate Bone Cements," *Orthopaedic Rev.*, 8(9): 41-44 (1979).
Bishop, N.E., et al., "Porosity Reduction in Bone Cement at the Cement-Stem Interface," *J. Bone Surg.*, 78-B(3): 359-356 (1996).
Topoleski, L.D., et al., "Microstructural Pathway of Fracture in Poly(methyl methacrylate) Bone Cement," *Biomaterials*,14(15):1165-1172 (1993).
Mapleston, P., "Broad Use Spectrum Seen for Microcellular Injection technique," *Modern Plastics* Dec.(1998). p. 31.
Schreurs,B.W., et al "Effects of Preparation Techniques on the Porosity of Acrylic Cements," *Acta Orthop Scand* 59(4):403-409 (1988).
Mëller-Wille, et al., "Integrated System for Preparation of Bone Cement and Effects on Cement Quality and Environment," *J. Biomed. Mat. Res.*, 38(2):135-42 (1997) Summer.
Knoell, A., et al, abstract, Ei Compendex®, "Graphite Fiber Reinforced Bone Cement," *Ann. Biomed. Eng.*, 3(2): 225-229 (1975).
Kindt-Larsen, Ture, et al. "Innovations in Acrylic Bone Cement and Application Equipment," *J. App. Biomater.*, 6:75-83 (1995).
Fritsch, E. W., "Static and Fatigue Properties of Two New Low-Viscosity PMMA Bone Cements Improved by Vacuum Mixing," *J. Biomed. Mat. Res.*, 31:451-456 (1996).
Connelly, T.J., et al., "The Role of Porosity in the Shrinkage of Acrylic Bone Cement," Trans 13th Mtg. Soc. Biomat, Jun. 2-6, New York, NY 1987.
Haas, S. S., et al., "A Characterization of Polymethylmethacrylate Bone Cement," *J. Bone Joint Surg.*, 57-A:380-391 (1975).
Sabokbar, A., et al., abstract Medline®, "Radio-Opaque Agents in Bone Cement Increase Bone Resorption," *J. Bone Joint Surg. Br.*, 79(1):129-134 (1997).
Lazarus, M.D., et al., abstract Medline®, "Comparison of the Inflammatory Response to Particulate Polymethylmethacrylate Debris With and Without Barium Sulfate," *J. Orthop Res.*, U.S., 12(4):532-541 (1994).
Topoleski, L.D., et al., abstract Medline®, "A Fractographic Analysis of in vivo Poly(methyl Methacrylate) Bone Cement Failure Mechanisms," *J. Biomed Mater Res.*, 24(2):135-154 (1990).
Nakahara, M., abstract Medline®, "An Objective Examination for Painful Hip After Total Hip Arthroplasty," *Acta Orthop. Scand.* 53 (4):591-600 (1982).

Rudigier, J., et al., abstract Medline®, "Release and Diffusion of Methylmethacrylic Monomers After the Implantation of Self Curing Bone Cements," *Unfallchirurgie*, 7(3):132-137 (1981).
Beaumont, P.W., abstract Medline®, "Fracture Processes in Acrylic Bone Cement Containing Barium Sulphate Dispersions," *J. Biomed Eng.*, 1(3): 147-152 (1979).
Rudigier, J., et al., abstract Medline®, "Biological Effect of Bariumsulfate as Constrast Material in Bone Cement," 86(3):279-290 (1976).
Friis, E.A., et al., abstract Ei Compendex®, "Fracture Toughness of Surface-Treated Carbon Fiber Reinforced Composite Bone Cement," *Transactions of the Annual Meeting of the Society For Biomaterials*, St. Louis Park, MN, USA, p. 913. (1996).
Lerouge, S., et al., abstract Medline®, "Characterization of in vivo Wear Debris From Ceramic-Ceramic Total Hip Arthroplasties," *J. Biomed. Mater. Res.*, 32(4):627-633 (1996).
Yoshida, K., and Greener, E.H., abstract Medline®, "Effects of Coupling Agents on Mechanical Properties of Metal Oxide-Polymethacrylate Compsites," *J. Dent.*, 22(1):57-62 (1994).
Hopf, C., et al., abstract Medline®, "Comparative Studies on the Radioactivity of Bone Cements Containing X-Ray Contrast Media and of the Contrast Media," *Rofo Fortschr Geb Rontgenstr Neuen Bildgeb Verfahr*, 152(5):601-200 (1990).
Streicher, R.M., et al., abstract Medline®, "New Surface Modification for Ti-6A1-7Nb Alloy: Oxygen Diffusion Hardening (ODH)," *Biomatarials*, 12(2):125-129 (1991).
Hopf, W., et al., abstract Medline®, "About Radioactivity in Some PMMA Bone Cements," *Acta Orthop. Belg.*, 56(2):443-444 (1990).
Gross, U., and Strunz, V., abstract Medline®, "The Interface of Various Glasses and Glass Ceramics With a Bony Implantation Bed," *J. Biomed. Mater Res.*, 19(3):251-271 (1985).
Bhambri, S.K., and Gilbertson, L.N., abstract Medline®, "Micromechanisms of Fatigue Crack Initiation and Propagation in Bone Cements," *J. Biomed. Mater Res.*, 29(2):233-237 (1995).
Owen, A.B., and Beaumont, P.W., abstract Medline®, "Fracture Behaviour of Commercial Surgical Acrylic Bone Cements," *J. Biomed Eng.*, 1(4):277-280 (1979).
Trieu, H.H., et al., "A Comparative Study of Bone Cement Preparation Using a New Centrifugation Mixing Technique," *The 20th Annual Meeting of the Society for Biomaterials*, Apr. 5-9, Boston, Massachusetts (1994).
Trehane, R.W., and Brown, N., abstract Medline®, "Factors Influencing the Creep Behavior of Poly(Methyl Methacrylate) Cements," *J. Biomed Mater. Res.*, 9(4): 81-88 (1975).
Imhof, A., and Pine, D.J., "Ordered Macroporous Materials by Emulsion Templating," *Nature*, 389(30): 948-951 (1997).
Pedley, R.B., et al., abstract Medline®, "Identification of Acrylic Cement Particles in Tissues," *Ann. Biomed. Eng.* 7 (3-4):319-328 (1979).
Demian, et al., "Regulatory Perspective on Characterization and Testing of Orthopedic Bone Cement," *Biomaterials*, 19:1607-1618 (1998).
Wu, S., "A Generalized Criterion for Rubber Toughening: The Critical Matrix Ligament Thickness ," *J. Appl. Polym. Sci.*, 35:549-561 (1988).
Charnley, J., "Anchorage Of The Fermoral Head Prosthesis To The Shaft of The Femur," *The J. of Bone and Joint Surgery*, 42-B:28-30 (1960).
Friis, E. A., et al., "Fracture Toughness Of Vacuum Mixed PMMA Bone Cement," *Transactions, Nineteenth Annual Meeting of the Society For Biomaterials*, Apr. 28-May 2, 1993, 16:301 (1993).
Skinner, H. B., et al., "Density Gradients In Bone Cement After Centrifugation," *Transactions, 31st Annual Meeting Orthopaedic Research Society*, Las Vegas, Nevada, Jan. 21-24, 1985, 10:243 (1985).
Gharpuray, V. M., et al., "Cracks Emanating From Circular Voids or Elastic Inclusions in PMMA Near a Bone-Implant Interface," *Transactions Of The ASME, J. Of Biomech. Engineer.*, 112(1):22-28 (1990).
Kurtz, S. M., et al., "Advances in the Processing, Sterilization, and crossliking of ultra-high molecular weight polyethylene for total joint arthroplasty," *Biomaterials*, 20(18):1659-1688 (1999).

Vila, M. M., et al., "Effect of Porosity and Environment on the Mechanical Behavior of Acrylic Bone Cement Modified With Acrylonitrile-Butadiene-Styrene Particles: I. Fracture Toughness," *J. Of Biomed. Materials Research*, 48:121-127 (1999).

Vila, M. M., et al., "Effect of Porosity and Environment on the Mechanical Behavior of Acrylic Bone Cement Modified With Acrylonitrile-Butadiene-Styrene Particles: Part II. Fatigue Crack Propagation," *Of Biomed. Materials Research*, 48:128-134 (1999).

Murakami, A., et al., "Rubber-modified Bone Cement," *J. Of Materials Science*, 23(6):2029-2036 (1988).

Puckett, A. D., et al., "Improved Orthopaedic Bone Cement Formulations Based On Rubber Toughening," *Critical Reviews In Biomed. Engineer.*, 28 (3&4): 457-461 (2000).

Kennedy, J. P., et al., "Polyisobutylene-toughened poly(methyl methacrylate): III. PMMA-*l*-PIB Networks As Bone Cements," *J. Of Biomaterials Sci., Polymer Edition*,4(5):445-449 (1993).

Moseley, J. P., et al., "The Development and Characterization Of A Fracture-Toughened Acrylic For Luting Total Joint Arthroplastics," *J. Of Biomed. Materials Research*, 47(4):529-536 (1999).

Kim, H. Y., et al., "Improvement Of Fatigue Properties of Poly(methyl methacrylate) Bone Cement By Means Of Plasma Surface Treatment Of Fillers," *J. Of Biomed. Materials Research*, 48(2):135-142 (1999).

Freitag, T.A., and Cannon, S.L., abstract Medline®, "Fracture Characteristics of Acrylic Bone Cements, I. Fracture Toughness," *J. Biomed. Mater Res.*, 10(5):805-828 (1976).

Holland, B.T., et al., "Synthesis of Macroporous Minerals With Highly Ordered Three-dimensional Arrays of Spheroidal Voids," *Science*,181:538-540, (1997).

Gilbert, J.L., and Ney, D.E., abstract, RAPRA Rubber & Plastics, "Self-Reinforced Composite PMMA: Static and Fatigue Properties," *Biomaterials*, 16(14):1043-1055 (1995).

Pourdeyhimi, B., et al., abstract, Ei Compendex®, "Comparison of Mechanical Properties of Discontinuous Kevlar 29 Fibre Reinforced Bone and Dental Cements," *J. Mat. Sci.*, 21(12):4468-4474 (1986).

James, S.P., et al., "A Fractographic Investigation of PMMA Bone Cement Focusing on the Relationship Between Porosity Reduction and Increased Fatigue Life," *J. Biomed. Mater. Res.*, 26:651-652 (1992).

Jasty, M., et al., "The Initiation of Failure in Cemented Femoral Components of Hip Arthroplasties," *J. Bone Joint Surg.*, 73(B):551 (1991).

Pourdeyhimi, B., et al., "Elastic and Ultimate Properties of Acrylic Bone Cement Reinforced with Ultra-High-Molecular-Weight Polyethylene," *J. Biomed. Materials Res.*, 23(1): 63-80 (1989).

Burke, D.W., et al., "Centrifugation as a Method of Improving Tensile and Fatigue Properties of Acrylic Bone Cement," *J. Bone Joint Surg.*, 66(A):1265-1273 (1984).

Davies, J.P., et al., "The Effect of Centrifuging Bone Cement," *J. Bone Joint Surg.*, 71(B):39-42 (1989).

Davies, J.P., et al., "Comparison of the Mechanical Properties of Simplex P, Zimmer Regular, and LVC Bone Cements," *J. Biomed. Mater. Res.*, 21:719-730 (1987).

Topoleski, L.D., et al., "The Effects of Centrifugation and Titanium Fiber Reinforcement on Fatigue Failure Mechanisms in Poly(methyl methacrylate) Bone Cement," *J. Biomed. Mater. Res.*, 29:299-307 (1995).

Lewis, G, et a., "Effect of Mixing Method on Selected Properties of Acrylic Bone Cement," *J. Biomed. Mater. Res.*, 38:221-227 (1997).

\* cited by examiner

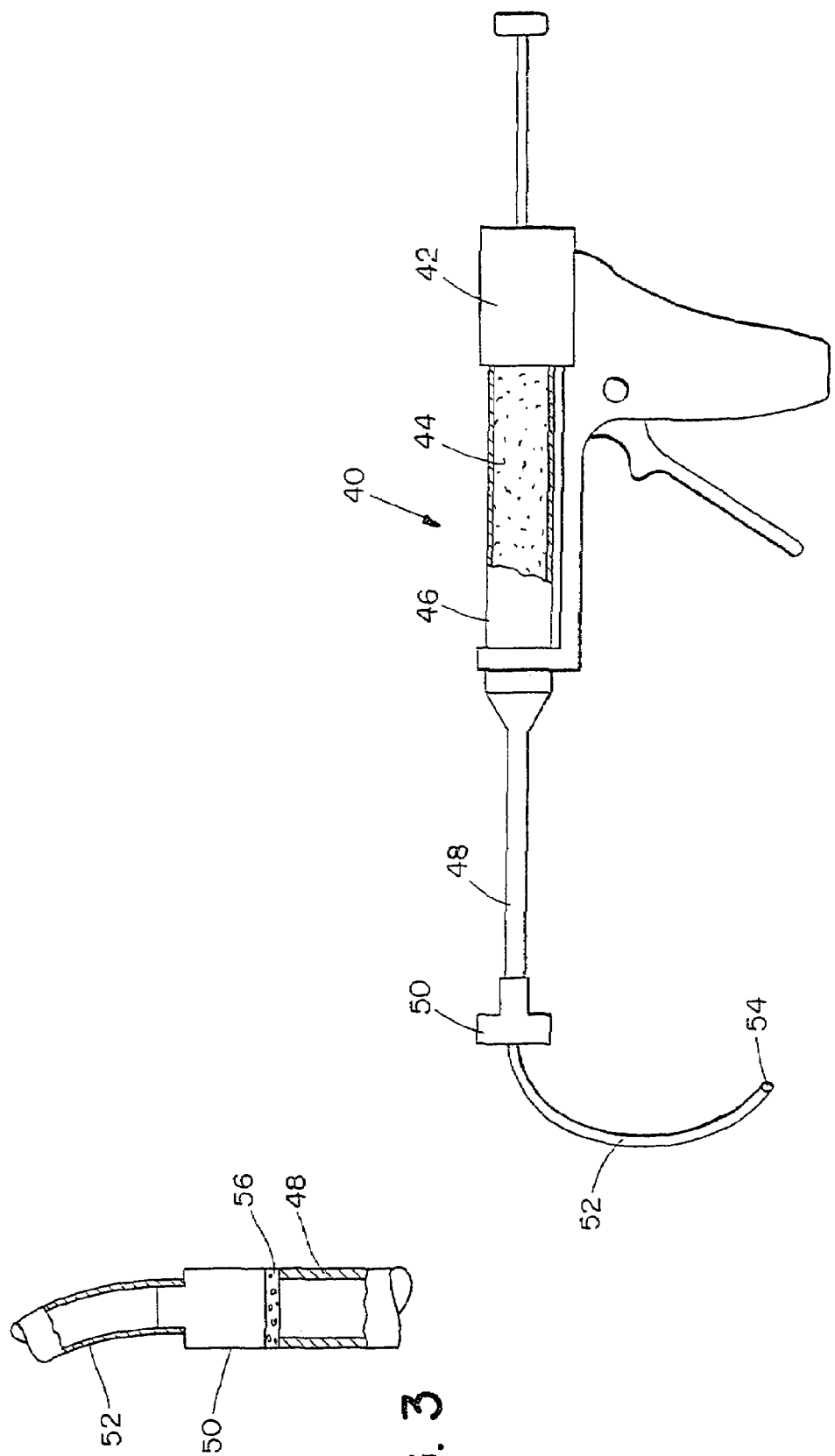

NANOCOMPOSITE SURGICAL MATERIALS AND METHOD OF PRODUCING THEM

RELATED APPLICATIONS

This application is a continuation of U.S. application Ser. No. 09/541,374, now U.S. Pat. No. 6,689,823, filed Mar. 31, 2000, which claims the benefit of U.S. Provisional Application No. 60/127,244, filed Mar. 31, 1999. The entire teachings of the above applications are incorporated herein by reference.

BACKGROUND OF THE INVENTION

Surgical materials are important synthetic biomaterials that can be implanted in humans or animals and are used extensively in orthopedic surgery and related areas such as total joint arthroplasty. A number of dental applications also require the use of surgical materials such as cements.

The most common cement currently employed in cemented total joint arthroplasty is obtained by the polymerization of poly(methyl methacrylate) with methyl methacrylate monomer. In cemented total joint replacement, the surgical cement, also referred to as the bone cement, anchors the prosthesis to the contiguous bone. One concern associated with self-curing acrylic-based bone cements is the fracture of cements due to defects such a voids and agglomeration of fillers. (Topoleshi LDT. et al, *Biomaterials* 14(15): 1166-1172 (1993) Microstructual Pathway of Fracture in Poly(Methyl Methacrylate Bone Cement (Demian, et al. Regulatory Perspective on Characterization And Testing of Orthopedic Bone Cement, *Biomaterials* 19: 160-7-1618 (1998). Accordingly, a need exists for surgical cements which eliminate or minimize the above-referenced problems.

SUMMARY OF THE INVENTION

The invention is directed to composite surgical materials characterized by a very fine matrix ligament thickness. The surgical material is referred to herein as a "nanocomposite material" as the material is characterized by a nanoscale structure produced by nanometer fillers. However, micron size fillers can be used in the materials and methods described herein. The average matrix ligament thickness of the composite surgical materials of the invention is less than about 1000 nanometers, preferably less than about 750 nanometers. More preferred are average matrix ligament thicknesses of less than about 500 nanometers. In an especially preferred embodiment, the surgical materials of the invention have an average matrix ligament thickness of less than about 250 nanometers. The reduced matrix ligament thickness of the surgical materials of the invention is promoted by both (a) fillers having a very fine average mass diameter and (b) dispersion methods which avoid or preclude filler aggregation or agglomeration.

The composite surgical materials of the invention include a polymer matrix (e.g., biodegradable or non-biodegradable polymer) and filler. In a preferred embodiment, the polymer matrix is obtained by the polymerization of poly(methyl methacrylate) with methyl methacrylate monomer. Other polymeric materials can also be employed.

The filler can be solid, liquid, gas or mixture thereof. The filler has an average mass diameter less than about 1000 nanometers, preferably less than about about 750 nanometers. More preferred are fillers having an average mass diameter of less than about 500 nanometers. In most preferred embodiments, fillers have an average mass diameter between about 1 nanometer and about 250 nanometers and in particular between about 1 nanometer and about 150 nanometers.

The invention also pertains to a polymeric powder for preparing a nanocomposite surgical material as described herein. A polymeric precursor (powder) is admixed with a filler to produce a uniformly dispersed polymeric powder. The powder can then be conveniently used in the preparation of a surgical material or cement. Preferably the polymeric powder includes polymethyl methacrylate.

The invention is also related to methods and apparatus for incorporating a filler in a polymer matrix and forming a composite surgical material having the reduced matrix ligament thickness discussed above. For an acrylic type surgical cement, the filler can be introduced into one of the cement precursors prior to mixing, during the mixing of the precursors or into a pre-prepared paste, dough or liquid where polymerization is induced. The filler is combined, dispersed or mixed into the cement in a way which minimizes the aggregation, agglomeration or coalescence of filler particles or filler domains such as filler droplets or bubbles.

One aspect of the invention is related to a method and apparatus wherein air-cement contact may be eliminated during storage, during transfer to the mixing chamber, during the mixing process, during the transfer from the mixing vessel to the syringe and to the nozzle, as well as during release at the in vivo site. In preferred embodiments of the invention, the methods and apparatus are used to incorporate the filler into the composite surgical materials discussed above.

The invention has many advantages. For example, the composite surgical material (e.g., surgical cements, plates and screws) of the invention have superior mechanical properties, in particular good toughness. The surgical materials prepared using the methods and apparatus of the invention are less likely to form the type of large voids which are thought to result in surgical material prone to fractures. The invention allows for the incorporation of small size, well dispersed fillers into the surgical material (e.g., surgical cements, bone cements, plates and screws). Fillers other than solid particles can be introduced into the composite surgical materials by practicing the invention. Since the invention can provide for the isolation or occlusion from ambient air of all steps involved in preparing and transferring the surgical material into a human or veterinarian patient, escape of harmful vapors or odors into the work environment is reduced or eliminated. If contact with air occurs at any of the steps, vacuum or a pressurizing gas can be reapplied.

BRIEF DESCRIPTION OF THE DRAWINGS

FIG. 2 represents a cross sectional view of an apparatus that can be used to pour the ready mixed cement into the nozzle.

FIG. 3 represents a cross sectional view of a vacuum nozzle adapter that can be used to apply a vacuum while dispensing the ready mixed cement into the nozzle.

Figure 1:
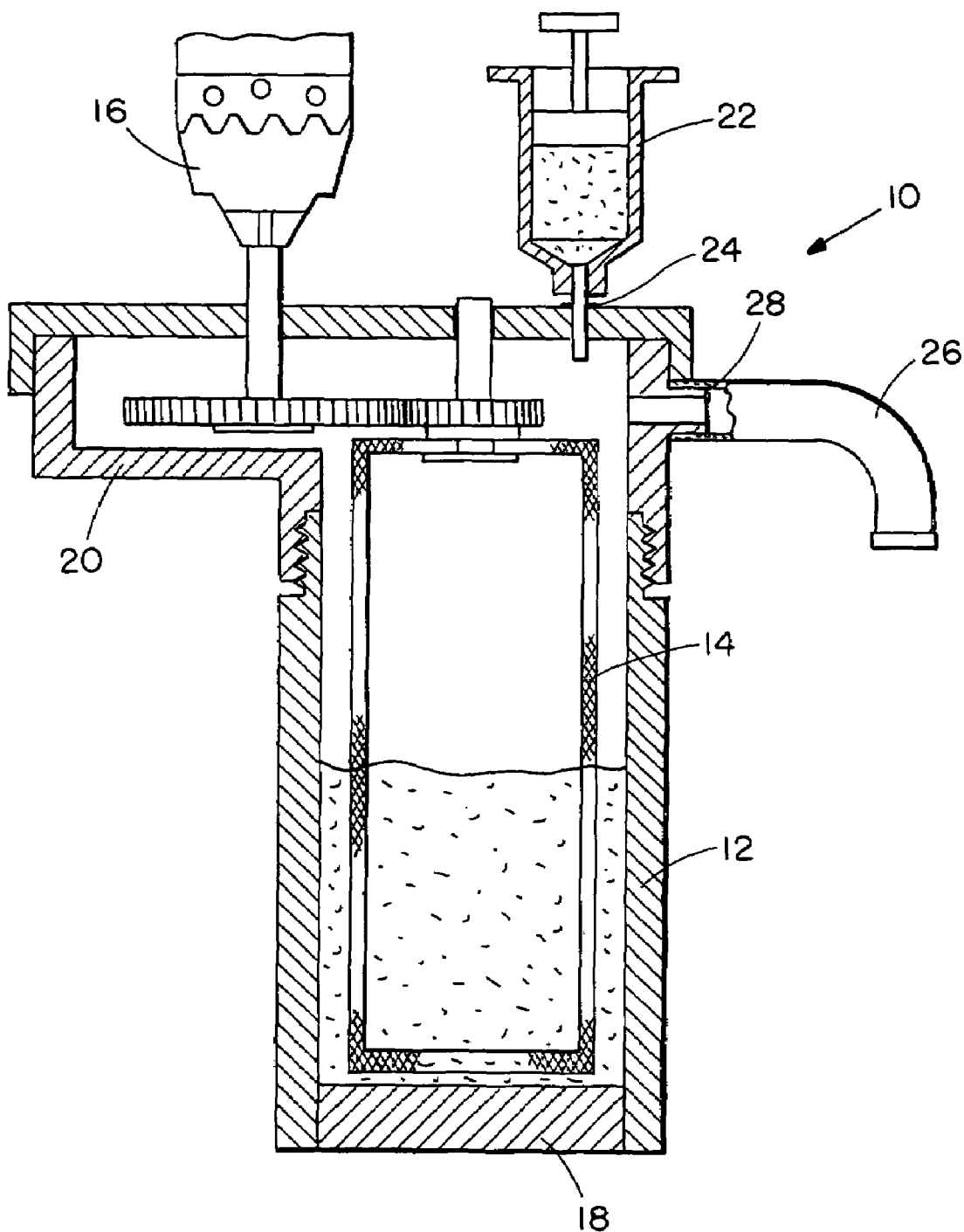
FIG. 1 represents a longitudinal cross-sectional view of a mixing apparatus that can be used to mix the cement precursors under vacuum or under pressure.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Surgical materials such as, for example, surgical (bone) cements, surgical implants, plates and screws, can include a polymeric matrix which can be formed from polymeric materials, e.g., non-biodegradable or biodegradable polymers. The invention can use any one of the materials currently employed in forming surgical cements. For example, the invention is directed to cements produced from non-biodegradable polymeric materials such as, for example, acrylic polymers, polyurethanes and others.

In a preferred embodiment, the composite surgical materials of the invention include acrylic-based polymers, in particular cements formed through polymerizing or curing poly(methyl methacrylate) and methyl methacrylate monomer. Precursors commonly used to produce self curing, acrylic type surgical cements, often include powder and liquid components. Powder components typically include prepolymerized poly(methyl methacrylate), an initiator for the polymerization reaction and a radio-opaque additive. Liquid components typically include methyl methacrylate monomer, a promoter or accelerator for breaking down the catalyst and for initiating free radicals and a stabilizer which prevents premature polymerization. Powder and liquid formulations suitable in forming acrylic surgical cements are commercially available, for example in quantities of 40 grams per package, and 20 ml per container, respectively.

In other embodiments, the polymer matrix of the surgical materials of the invention can also include methyl methacrylate and/or its co-polymers such as methyl methacrylate-co-styrene, polymerized butyl methacrylate, styrene, carbonate and others. Residual monomer such as methyl methacrylate or butyl methacrylate can also be present in the polymer matrix.

In further embodiments, pre-prepared pastes, doughs or liquids can be employed. Often, the curing of these viscous formulations is induced (or their rate of polymerization is increased), as desired for application at the in vivo site. Other suitable formulations for producing bone cements include but are not limited to polyurethanes.

In another embodiment, surgical materials include ploymers that are biodegradable. Resorbable polymers are particularly useful in fabricating implant plates and screws and can include, for example, polylactic acid (PLA), polyglycolic acid (PGA), polydioxanone (PDS), polyethylene oxide (PEO) polycaprolactone (PCL), as well as co-polymers or blends thereof. The invention can also be practiced with cements used in dental applications, art restoration and other fields.

The surgical materials of the invention (e.g. bone cements, prepolymerized surgical implants, plates, screws) also include a filler. The filler can be solid or fluid (a liquid, or a gas). Mixtures of components of different chemical compositions and mixtures of solids, mixtures of fluids and mixtures of solids and fluids can also be employed.

In preferred embodiments of the invention, the fillers employed deliver additional benefits. For example, fillers can have radio-opaque properties or can include biologically active or pharmaceutical compounds, such as, for example, bisphonates, antibiotics and others. Other preferred fillers include fillers which have magnetic properties and can create or enhance a magnetic field. Still other preferred fillers which can be employed have osteoinductive properties. Fillers also can include biologically active substances such those used in the treatment, prophylaxis or diagnosis of diseases. Specific examples include but are not limited to growth factors, bisphonates, antibiotics and others. Solid biomolecules and pharmaceutical compounds (e.g., gentamicin, tobramicin) also can be used as fillers.

In a preferred embodiment, the solid fillers employed have X-ray contrast properties. Examples of fillers which have X-ray contrast or radio-opaque properties include but are not limited to barium salts, such as, for example, barium sulfate, barium fluoride and barium polyacrylate; metal oxides, such as, for example, titanium dioxide, zirconium oxide, chromium oxide, and zinc oxide; bismuth glass; and mixtures thereof. Such compounds are also referred to herein as radio-pacifiers. Examples of other solid fillers include, but are not limited to carbon particles, solid organic or polymeric compounds, such as thermoplastics, thermosets, elastomers or rubbers, (for example: poly dimethyl siloxane), glassy polymers (for example: polystyrene latex particles), block copolymers (for example: poly (methyl methacrylate-co-dimethyl siloxane) are still other solid fillers which can be used in practicing the invention. Fillers which incorporate pharmaceutical powder formulations can also be employed.

Liquid fillers can include pure liquids (for example: water, ethanol), mixtures of liquids or liquids containing dissolved chemicals. In a preferred embodiment, the liquid filler includes a bioactive material dissolved, dispersed, suspended or otherwise combined with the liquid. For example, biomolecules or pharmaceutical compounds used in the prophylaxis, treatment or diagnosis of disease, such as peptides, proteins, antivirals, antibiotics solutions or suspensions can be employed. Specific examples include but are not limited to alendronate dissolved in either water or alcohol, colloidal hydroxyapatite particles suspended in water.

Gaseous fillers include but are not limited to air, carbon dioxide, oxygen, nitrogen, argon, xenon, krypton and other gases and mixtures thereof.

As noted above, the invention can be practiced with mixtures of fillers having different compositions and/or phase. For example, two or more chemically different gas, solid or liquid fillers can be incorporated into the polymer matrix. Micelles containing aqueous or non-aqueous liquids or mixtures of liquids or solutions or dispersions of pharmaceutical compounds and micelles formed from block copolymers (for example, poly(dimethyl siloxane and ethylene glycol copolymers), synthetic amphiphilic molecules (bis(2-ethylhexyl)sulfosuccinate, for example) or biological amphiphilic molecules (L-alpha-phospatidylcholine, for example) can also be used, as can solid hollow microspheres having a solid shell which may be polymeric and which surrounds a gas, liquid or solid core.

The invention is related to building into surgical materials a very fine heterogeneous structure formed by incorporating into the polymer matrix one or more well dispersed, small size fillers, preferably nanometer size fillers. In the surgical materials of the invention, filler particles or filler domains give rise to a fluctuation in density or composition. As used herein, the term "fluid filler" refers to gaseous fillers or to liquid fillers and the terms "filler particles" and "filler domains" are used herein in relation to solid fillers and to fluid fillers, respectively. The shortest distance between the closest surfaces or closest outer edges of two neighboring filler particles or filler domains represents the "matrix ligament thickness" or, in short, the "ligament thickness".

The composite surgical materials of the invention are characterized by an average matrix ligament thickness, defined as the average shortest distance between the closest outer edge or surface of neighboring filler particles, filler domains or their agglomerates, which is less than about 1000 nanometer. Preferably, the average matrix ligament thickness less than about 750 nanometers. More preferred are average matrix ligament thicknesses of less than about 500 nanometers. In an especially preferred embodiment, the surgical materials of the invention have an average matrix ligament thickness of less than about 250 nanometers. As used herein, the phrase "low matrix ligament thickness" refers to an average matrix ligament thickness which is less than about 1000 nanometers.

Matrix ligament thickness is discussed, for example, by S. Wu, *J. Appl. Polym. Sci.*, Vol. 35:549-561 (1988), the contents of which are incorporated herein by reference in their entirety. Matrix ligament thickness can be estimated by applying the following mathematical equation which relates the matrix ligament thickness to the diameter of particles in a heterogeneous material when the particles are uniformly dispersed in the matrix material:

$$\tau = d[k(\pi/6\phi)^{1/3} - 1]$$ Equation 1 where $\tau$ is the matrix ligament thickness, d is the particle diameter, $\phi$ is the volume fraction of the particles in the polymer matrix and k is a geometric constant related to particle packing. For example, for a cubic lattice, k=1, for a body centered lattice, $k=2^{1/3}$, and for a face centered lattice, $k=4^{1/3}$.

Equation 1 can be employed also to calculate matrix ligament thickness for fluid (gas or liquid) fillers.

Matrix ligament thickness can also be determined experimentally, for example from micrographs obtained by electron microscopy techniques, for example by scanning electron microspcopy or SEM. Image analysis techniques, such as, for example, Scion Image 1.6, can be employed to estimate the matrix ligament thickness from given SEM micrographs. Ultra small angle X-ray scattering (USAXS) is another suitable experimental technique which can be employed to determine matrix ligament thickness.

The use of small diameter filler particles or domains promotes low ligament thickness, such as a ligament thickness which is less than about 1000 nanometers, hence the preference for small average diameter fillers. In addition, low matrix ligament thickness is also enhanced by employing methods of combining, mixing or dispersing which minimize the aggregation, agglomeration or coalescence of filler particles or filler domains (bubbles or droplets). In turn, this minimizes formation into the surgical material structure of large pores, corresponding to filler aggregates, and is believed to reduce mechanical failure and aseptic loosening incidents.

The fillers employed in the practice of the invention have an average mass diameter of less than about 1000 nanometers, preferably less than about 750 nanometers. More preferred are fillers having an average mass diameter of less than about 500 nanometers. In most preferred embodiments, fillers have an average mass diameter between about 1 nanometer and about 250 nanometers and in particular between about 1 nanometer and about 150 nanometers. As used herein, the term "mass diameter" refers to the longest dimension of the cross-sectional area of the filler solid particle, liquid droplet or gaseous bubble. For a spherical particle, droplet or bubble, the mass diameter is the same as the diameter of the sphere. For nano-fibers or nano-tubes, the mass diameter is the thickness of the fiber or tube.

Incorporation of a filler into the polymer matrix generally is carried out at a point prior to the setting of the material. For example, fillers can be combined, incorporated, included or otherwise mixed with a powder precursor employed in making a surgical cement, such as for example, a powder which includes the prepolymerized poly(methyl methacrylate). Fillers can also be incorporated, for example, solubilized or dispersed into a liquid precursor, for example, in the liquid methyl methacrylate monomer formulation. The filler can also be incorporated into the bone cement by adding it to both powder and liquid precursors before or during mixing the components. Alternatively, the filler can be incorporated into a pre-prepared paste, dough or liquid for which curing can be induced (or rate of curing can be increased) prior to the complete curing or setting of the cement.

Depending on how the filler is combined with precursor materials employed in forming the polymer matrix of the surgical materials of the invention, those skilled in the art will recognize that regions of higher filler concentration and regions from which filler may be absent may exist in the polymeric matrix. For instance, a surgical cement formed by combining a filler, such as, for example, a radio-opaque compound, with a poly(methyl methacrylate) powder, followed by combining the mixture with a liquid component (e.g., methyl methacrylate monomer), followed by curing, can display regions which include the filler and correspond to the polymerized monomer and regions which correspond to the pre-polymerized powder particles, in which filler is absent. Such regions can be observed by electron microscopy techniques, as known by those skilled in the art. In such instances, matrix ligament thickness or average matrix ligament thickness of the surgical materials of the invention are determined in the regions which include filler, e.g. the regions formed corresponding to the filler/polymerized monomer described above.

In another embodiment, a filler can be present in a liquid precursor (e.g. methyl methacrylate monomer) but not in the powder precursor. In this case, filler is predominantly present in regions corresponding to polymerized monomer. Matrix ligament thickness or average matrix ligament thickness are determined in regions formed by polymerized monomer. In yet another embodiment, a filler can be present within the pre-polymeric powder particles.

Low matrix ligament thicknesses are promoted also by minimizing filler agglomeration or aggregation. Methods which can be employed in enhancing filler dispersion and minimizing agglomeration or aggregation are described below.

Uniform dispersions of fillers can be obtained by employing mechanical means (e.g., high speed mixing, ultrasonication) or by other techniques, such as, for example, applying electrostatic forces. Both solid nanoencapsulated fillers, such as those described below, as well as uncoated solid fillers can be used.

In one embodiment of the invention, solid filler is dispersed in a powder precursor of a surgical material by mixing the filler and powder precursor at a stirring rate exceeding about 350 rpm, preferably is in excess of 500 rpm, for example, it can be in the range from about 750 to about 2,000 rpm and as high as about 2,000 to about 20,000 rpm. As used herein, "stirring rate" corresponds to the rate at which the axle of the stirrer rotates. In a preferred embodiment filler particles have an average mass diameter of less than about 1000 nanometers. Uniform dispersion can also be imparted to larger fillers, for example fillers having an average mass diameter in the range between 1 and 100 microns.

Other methods suitable to uniformly disperse solid fillers in a precursor component employed in producing the surgical materials of the invention include, but are not limited to, ultrasonication and the use of electrostatic forces to minimize or essentially eliminate aggregation. Techniques for performing ultrasonication and or applying electrostatic forces are known in the art.

Other methods for preventing or reducing agglomeration or aggregation of filler particles include the use of dispersing agents. Dispersing agents can be used in addition to or alternatively to the mechanical means of mixing, (e.g., high rates of mixing, ultrasonication) or to employing electrostatic forces, such as, for example, described above.

In one embodiment, the dispersion of a solid filler in one of the precuror materials employed to form the surgical materials of the invention, for example into the powder component employed to form a polymerized acrylic cement, can be enhanced by treating the solid filler with a dispersing agent which reduces the agglomeration or aggregation of filler particles. Dispersing agents can be used, for example, during fabrication of the pre-polymerized powder, and to facilitate the introduction of fillers into the powder such that the average ligament thickness of the resulting surgical material is less than about 1000 nanometers, preferably in the range of about 1 nanometer and about 750 nanometers. Examples of compounds which can be employed to treat solid filler particles to increase their dispersion properties, to reduce their agglomeration or aggregation and enhance the uniformity of dispersion include but are not limited to organic compounds, such as, for example, the monomer used to make the surgical materials of the invention, citrates and others. Coupling agents such as organosilanes can be employed also, as can be polymeric materials such as surfactants, for example sodium dodecyl sulfate.

Preferably, the solid filler particles are impregnated or thinly coated with the dispersing agent. Layers which are less than about 1000 nanometers, in particular layers in the range of 1 nanometer to 750 nanometers are preferred resulting in fillers which are referred to herein as "nanoencapsulated". Especially preferred are fillers impregnated with a monolayer-thin dispersing agent.

Methods of treating solid fillers with dispersing agents are known in the art. For example, solid fillers can be combined with an agent such as described above in a colloidal solution, followed by drying.

In one embodiment of the invention, water-oil emulsions using micelles can be formed in the liquid monomer and then combined with the pre-polymerized powder precursor.

In another preferred embodiment, a suspension of filler is formed in the liquid monomer and then combined with the powder.

Dispersing can be carried out using a dispersing agent or a surfactant, such as an amphiphilic molecule that includes a hydrophilic portion and a hydrophobic portion. Examples of preferred surfactants include but are not limited to synthetic commercial surfactants such as (1) IGEPAL™ (Rhodia Inc., Cranbury, N.J.) which are nonylphenol ethyxylates; (2) AOT, the chemical name for which is bis(2-ethylhexyl) sulfosuccinate; and (3) CTAB which is hexadecyltrimethylammonium bromide. In a preferred embodiment, biological amphiphilic molecules are used as dispersing agents, such as phospholipids (for example, L-alpha-phosphatadylcholine and other phosphatidylcholines, phosphatidylethanolamines, phosphatidylglycerols, phosphatidylserines, phosphatidylinositols and combinations thereof).

In one formulation, a known amount of dispersing agents is dissolved into the monomer, followed by addition of water or another liquid filler that is immiscible with the monomer, resulting in a water-in-oil type of microemulsion in which the water domains are of a diameter in the range of less than about 1000 nanometers, preferably less than 750 nanometers and can be as small as about 1 nanometer. This monomer nanoemulsion is mixed with polymer powder and polymerized to form the final surgical material.

In another embodiment of the invention, a gaseous filler is dispersed into a liquid, a mixture of powder and liquid precursors, or into a pre-prepared paste, dough or liquid where polymerization is induced or where the rate of polymerization is increased, prior to use, by dispersing at variable speed in a gaseous atmosphere. The pressure of the gaseous atmosphere can vary from dispersing under vacuum to dispersing at atmospheric or at higher than atmospheric pressures. Dispersing can also be carried out under fluctuating pressure conditions. For example the pressure can be changed, increased and/or relaxed one or several times or alternated at regular or varied time intervals. The pressure fluctuations can range from vacuum pressures to pressures exceeding atmospheric pressure.

The amount of filler that is to be added in order to obtain the desired mechanical properties and minimal ligamant thickness depends on at least some of the following parameters: the type of filler, the cement composition, the dispersing techniques and/or apparatus. The optimum amount of filler can be determined experimentally. A filler such as water, for example, has been dispersed up to 40% (by volume) in monomer using a mixed surfactant system.

The surgical materials of the invention can be thought of as "composites" since they include chemically distinct components: a polymer matrix such as the self-curing acrylic material (for instance, polymerized poly(methyl methacrylate) with methyl methacrylate monomer) and a filler. Though each component has its own physical and chemical properties, when combined, the result is a surgical cement material having properties that are different from those of either component. Composites are often associated with improved mechanical properties. Since the surgical materials of the invention are characterized by small matrix ligament thicknesses, often on the nanometer scale, they also can be referred to as nanophase composites or nanocomposites.

Mechanical properties of the composite surgical materials of the invention can be tested as known in the art. Specific mechanical properties which can be tested include, for example, tensile failure stress, tensile modulus, fracture toughness, breaking stress and strain, and others. Preferred testing methods include, for example, ASTM (American Society for Testing & Materials) standard compression test, as specified under the jurisdiction of ASTM Committee F-4 on Medical and Surgical Materials and Devices and designated by the number F 451-95; ASTM Compact Tension Tests Protocol specified under the article D 5045-96 ("Standard test methods for plane-strain fracture toughness and strain energy release rate of plastic materials"); ASTM Standard D 638 tensile tests; and ASTM Standard Test Method for Measurement of Fatigue Crack Growth Rates, designation E647-95a and useful for long term mechanical testing.

Another aspect of the invention is related to methods and apparatus for preparing surgical cements. The methods and apparatus of the invention can be used to eliminate air contact during the storage of cement precursors, during the mixing process, during transfer from the mixing chamber into a syringe/nozzle device and during release to the in vivo site, for example into the intramedullary canal. In a preferred embodiment, the methods and apparatus of the invention are used to incorporate fillers and to form the composite surgical materials discussed above. In a particularly preferred embodiment, high speed mixing can be simulataneously applied.

In one embodiment of the invention, the cement precursors are stored under vacuum before being mixed, are mixed under vacuum, are transferred into the discharge chamber (also referred to herein as a syringe or a gun) under negative pressure, introduced into the nozzle under vacuum and released into the in vivo site. If the vacuum is broken at any of these steps, it can be reapplied using the apparatus and methods of the invention. An inert coolant such as dried ice or liquid nitrogen can be used to avoid frictional heating due to high speed mixing.

Alternatively, pressure can be substituted for vacuum during all or part of the mixing and/or transfer process. Gases other than air, for example nitrogen, carbon dioxide or a rare gas can be used to provide a positive, atmospheric or lower than atmospheric pressure during some or all stages of storing, mixing, transfer and delivery process. If air contact occurs at any of the steps, the gas pressure can be reapplied, using the apparatus and methods of the invention.

A schematic diagram of an apparatus which can be employed to carry out the invention is shown in FIG. 1. FIG. 1 shows cement mixer 10 which includes container 12. Container 12 can be constructed from a suitable material such as, for example, stainless steel, or thermoplasts or other. Materials which do not react with the cement precursors, mixtures thereof, or their reaction products are preferred. In one embodiment, container 12 is fabricated to withstand pressures higher than atmospheric.

Container 12 includes stirrer 14 which is connected to driving motor 16. Optional transmission means between stirrer 14 and motor 16 (not shown in FIG. 1), such as gear mechanisms or through one or more rotating spindles, as known in the art, can be employed. In one embodiment of the invention, stirrer 14 can be constructed from multiple fine wires. Preferably the wires have a diameter of less than 1 millimeter. Stirrers including paddles, blades, impellers, such as, for example, helical impellers, beater rotors or rotor turbines can also be employed.

Driving motor 16 can be, for example, a surgical drill or another motor known in the art. Preferably, driving motor 16 provides for rates of mixing corresponding to a stirring at a rate (corresponding to the rate of rotation of stirrer axis) in excess of about 750, for example up to about 1250 rpm (rotations per minute). It can be as high as 2000 to 20000 rpm.

Container 12 also includes piston 18 which can be employed to release the contents of container 12, preferably after mixing. In one embodiment, piston 18 is a plug such as a piston for a cement gun, further described below. Piston 18 can be moved on stirrer 14 axis thus opening a passageway to a syringe/nozzle assembly which is further described below. Preferably, the syringe/nozzle assembly is located adjacent to container 12 and vacuum is maintained in container 12 as well as in the syringe/nozzle assembly.

Container 12 also includes lid 20 which can be adapted to receive cement precursors from optional dispenser 22, through conduit 24. Preferably, lid 20 is fitted to container 12 in a leak tight manner which allows container 12 to remain under vacuum. In one embodiment, conduit 24 is fitted to lid 20 and optional dispenser 22 in a manner designed to withstands a positive pressure. In a preferred embodiment, conduit 24 includes a port connector designed for a standard syringe used in the health care industry.

As in the case of container 12, dispenser 22, if used, is constructed from materials which do not react with the chemical compounds enclosed therein. Preferably, optional dispenser 22 is constructed from materials and in a manner designed to maintain a vacuum and/or withstand a positive pressure. More than one dispenser 22 can be employed, as can be industry provided container of several units. For example, for preparing a self-curing acrylic cement, lid 20 can be adapted to receive a liquid monomer precursor from a first dispenser 22 and a solid powder precursor from a second dispenser 22 (not shown in FIG. 1). Alternatively, the liquid monomer and the powder dispenser can be combined in one dispenser 22. A solid, liquid or gaseous filler, such as the fillers described above, can be combined with the contents of dispenser 22. In other embodiments, an additional dispenser, optionally similar in design to dispenser 22, can be employed to contain and release to container 12 a solid, liquid or gaseous filler such as the fillers described above.

Container 12 can be subjected to the application of vacuum or of a gas, such as, for example, the gas described above, employing hose 26. Pressurizing gas can be applied continuously or intermittently. Vacuum and pressurization of cement mixer 10 can be alternated. In a preferred embodiment, a rapid increase or a rapid decrease in pressure is employed. The vacuum can range between 5 and 25 inches of Hg. Pressures, such as, for example, pressures higher than 25 inches of Hg, atmospheric pressure or pressures up to several bars can be employed. If pressures higher than atmospheric are employed, a safety relief valve, not shown in FIG. 1 is provided to cement mixer 10, as known in the art.

Components present in container 12 are mixed, preferably by the high speed mixing described above. In one embodiment of the invention, the contents of dispenser(s) 22 can be released into container 12 where they are mixed. A vacuum or a desired gas atmosphere can be sustained in the mixing area and discharge/nozzle assembly. Vacuum or gas can be re-applied if air contact takes place.

Once mixing has been completed, the ready mixed cement is ready to be applied to the desired bone site. This is generally accomplished by using a tube or nozzle which provides a conduit to the in vivo site as would be known to one skilled in the art. In the event that the mixture becomes exposed to ambient air during this stage of the process, vacuum (or gas) can be reapplied.

In one embodiment of the invention, once mixing is completed, piston 18 is moved upwards by pulling on the stirrer axis thus opening a passageway into the syringe/nozzle assembly which is positioned next to the mixing device. A continuous vacuum can be maintained in the mixing area and in the discharge/nozzle assembly (FIGS. 2 and 3). In another embodiment of the invention, transport of the mixed material is carried out under vacuum to the tip of the applicator through a vacuum hose.

After completion of the cement transfer, the plunger is moved downwards to transfer the plug into the syringe. The cement settles in the syringe under vacuum and then into the tip of the evacuated nozzle. Lastly, the syringe/nozzle device is removed from the holding device and placed in a cement gun.

FIG. 2 shows assembly 40 which includes cement gun 42. Cement gun 42 allows the contents 44, enclosed in syringe 46 to be pushed through conduit 48 through vacuum nozzle adapter 50. Hose 22 is connected to vacuum 54 and allows for applying a vacuum to assembly 40. FIG. 3 shows a more detailed schematic diagram of vacuum nozzle adapter 50 which includes membrane 56. Membrane 56 allows for gas to be evacuated from assembly 40 but prevents contents 44 from being transferred into hose 52. Membrane 56 may be replaced by a porous rod. For example, the solid non-porous rod currently used in mixing devices can be replaced with a porous rod. In a preferred embodiment, nozzle 48 is assembled to container 12 of FIG. 1, vacuum (50-52) is applied, and loaded in cement gun 40.

The invention will now be further explained in the following examples which are not intended to be limiting. All parts and percentages are by weight unless otherwise stated.

EXEMPLIFICATION

EXAMPLE 1

The fabrication and mechanical properties were studied for surgical cements that contain particulate fillers dispersed into the cement with various matrix ligament thicknesses. The cement compositions that were tested were: CMW1™ obtained from Johnson & Johnson/Dupuy Inc., located in Warsaw, Ind., SIMPLEX P® obtained from Stryker Howmedica Osteonice Inc., located in Rutherford, N.J. and also cement powder and monomer obtained from Esschem Inc., located in Linwood, Pa. The cements tested were based on prepolymerized poly(methyl methacrylate) and a copolymer of poly (methyl methacrylate-co-styrene). The filler particles tested were barium sulfate powder of 1-3 micrometer diameter which are packaged separately along with CMW1™ cement obtained from Johnson & Johnson/Depuy Inc. Barium sulfate powder of 100 nanometer diameter obtained from Sachtleben Chemie, Duisburg, Germany and NANOTEK™ alumina powder of 60 nanometer in diameter obtained from Nanophase Technologies Corporation, Burr Ridge, Ill. were also employed. In the case of the 100 nanometer size barium sulfate powder, the particles were coated with sodium citrate. In the case of 60 nanometer size alumina powder, the particles were coated with an acrylic coating. The purpose of the coatings was to prevent agglomeration of the particles in the cement upon mixing.

For all barium sulfate containing cements, the weight fraction of the particles based on the total weight of the cement was 10 wt %. In the case of the alumina containing cement, the volume fraction of the alumina particles was matched with that of the barium sulfate containing cements.

The cements were mixed under standard vacuum mixing conditions using an ARTISAN™ mixer obtained from Stryker Howmedica Osteonics Inc., Rutherford, N.J. The monomer was prechilled to 6° C. prior to mixing. An ARTISAN™ cement gun was used to apply all mixed cements into molds for mechanical testing.

Tensile testing was performed according to ASTM Standard D 638 with a Type V dog-bone specimen. Dimensions of the gage section were: width 3.18 mm, thickness 4 mm, length 7.62 mm.

A minimum of 4 samples were tested on an INSTRON 4201 universal testing machine with a crosshead speed of 1 mm/min until failure. Data sampling occurred at a rate of 20 Hz for both displacement and load. The work-of-fracture was calculated from the stress-strain data and is presented in Table 1. The units of measurements are:

Work-of-fracture (WOF): [$MJ/m^3$]

Table 1 shows that the work-of-fracture (WOF), which is a measure of energy required to break, was the highest for the Esschem cement containing the 60 nanometer size nanoencapsulated (coated) alumina particles and for the CMW1™ cement containing the 100 nanometer diameter, sodium citrate coated barium sulfate particles. Thus, the toughness of these cements was higher than the 1-3 micrometer diameter barium sulfate containing Esschem, CMW1™ and SIMPLEX™ cements. In addition, Table 1 shows results obtained by employing high speed mixing with uncoated fillers.

TABLE 1

| Sample | mean work-of-fracture | standard error of the mean |
| --- | --- | --- |
| Radiolucent Control | | |
| CMW1 radiolucent | 2.77 | 0.26 |
| Radiopaque Controls | | |
| Esschem PMMA + 10 wt. % BaSO4 | 1.78 | 0.26 |
| CMW1 radiolucent + 10 wt. % BaSO4 | 1.72 | 0.19 |
| Simplex P (including 10 wt. % BaSO4) | 2.30 | 0.20 |
| Nanocomposites | | |
| Esschem + uncoated Al$_2$O$_3$ | 2.01 | 0.13 |
| Esschem + nanoencapsulated Al$_2$O$_3$ | 3.09 | 0.31 |
| 600 nm uncoated | 2.21 | 0.13 |
| 600 nm nanoencapsulated | 2.05 | 0.16 |
| 100 nm uncoated | 2.36 | 0.24 |
| 100 nm nanoencapsulated | 2.94 | 0.25 |
| High-Speed Mixing | | |
| 600 nm uncoated Turbo | 2.17 | 0.05 |
| 100 nm uncoated Turbo | 4.61 | 0.10 |

EXAMPLE 2

Equation 1 (Wu, 1988) can be employed to relate the matrix ligament thickness to the diameter of particles in a heterogeneous material when the particles are uniformly dispersed in the matrix material:

$$\tau = d[k(\pi/6\phi)^{1/3} - 1]$$ Equation 1 where $\tau$ is the matrix ligament thickness, d is the particle diameter, $\phi$ is the volume fraction of the particles in the polymer matrix and k is a geometric constant. For a cubic lattice, k=1, for a body centered lattice, k=$2^{1/3}$, and for a face centered lattice, k=$4^{1/3}$.

The weight fraction of filler particles in the monomer phase was 16.6%. Based on the density of barium sulfate of 4.2 g/cc and a density of 1.2 g/cc for polymethyl methacrylate, the volume fraction of barium sulfate in the cured methyl methacrylate monomer phase of all cements was 5.4. Based on the density of aluminim oxide of 4.0 g/cc, the volume fraction of alumina in the cured methyl methacrylate monomer phase was 5.7. Table 2 shows the matrix ligament thickness calculated using equation 1 for barium sulfate and alumina for the respective particle diameters, and assuming a cubic lattice where the matrix ligament thickness is minimum compared to the cubic and body centered lattices. No agglomeration of particles in the cements was assumed.

TABLE 2

| Particle Composition | Particle Diameter (nanometer) | Matrix Ligament Thickness (nanometer) |
|---|---|---|
| Barium sulfate | 2000 | 2265 |
| Barium sulfate | 100 | 113 |
| Aluminum oxide | 60 | 66 |

Figure 4:
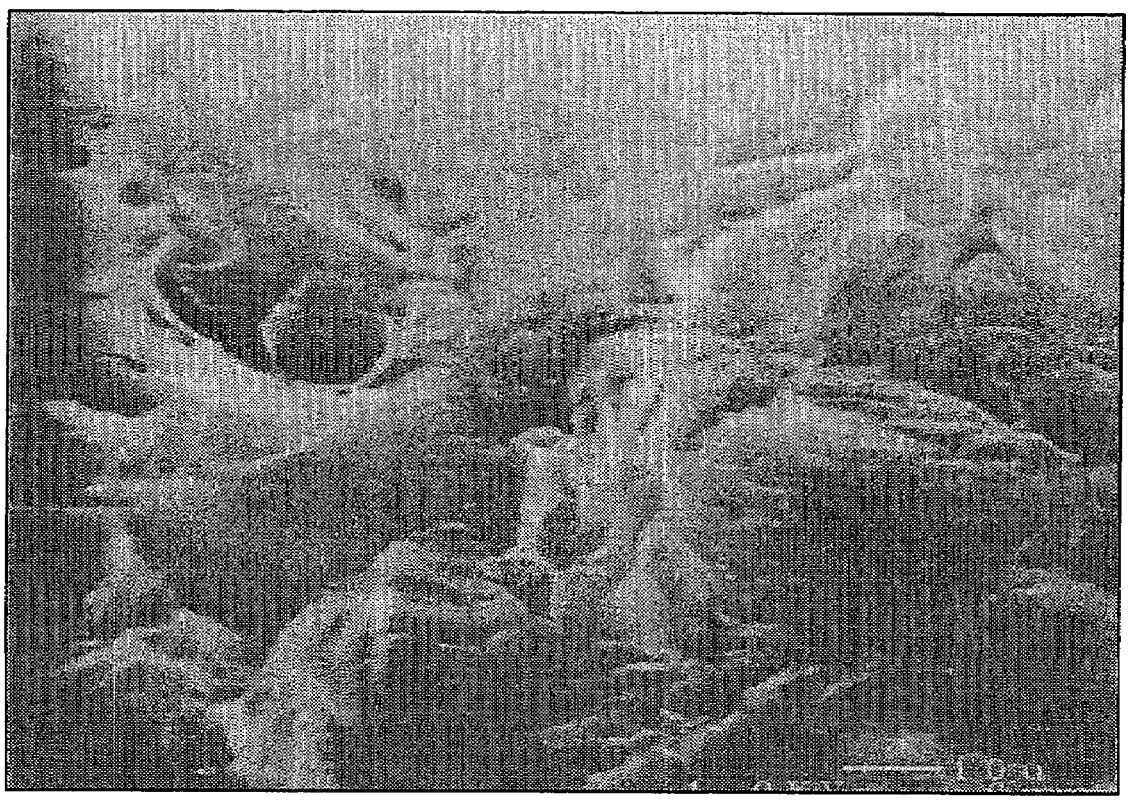
FIG. 4 is a scanning electron microscopy (SEM) micrograph of a radiolucent cement containing no filler.
Figure 5:
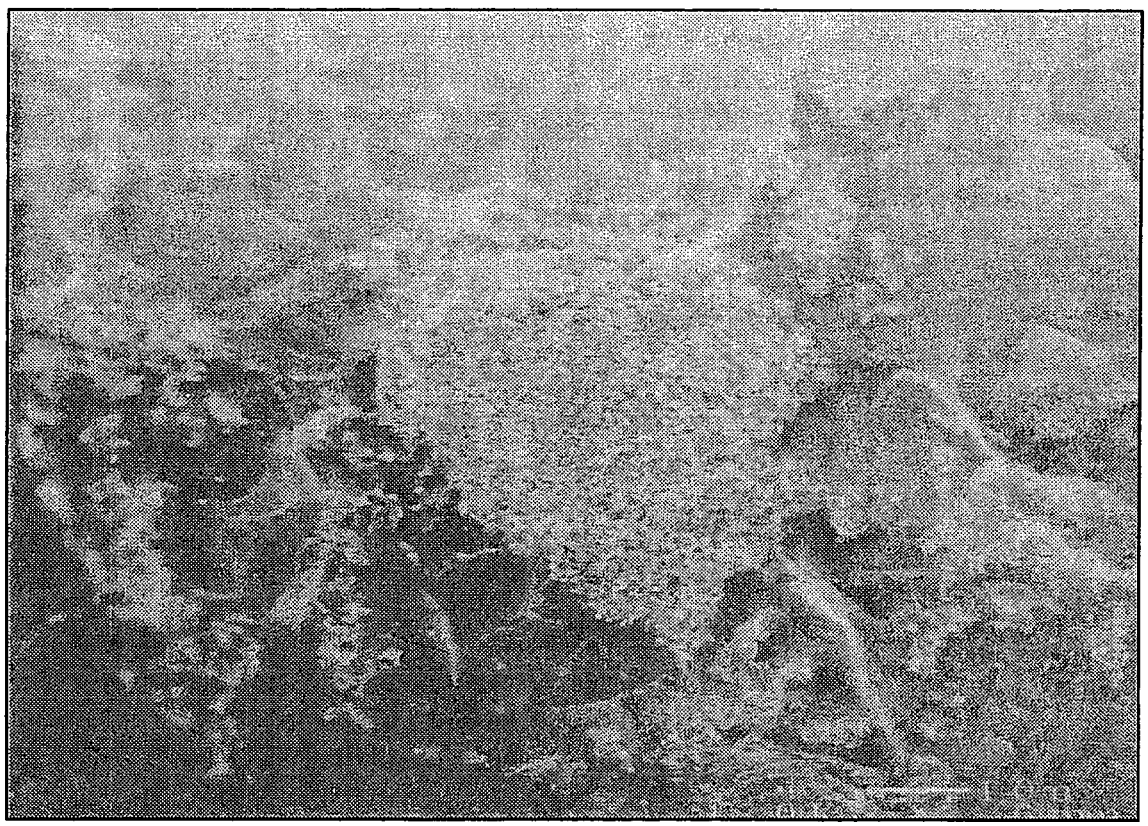
FIG. 5 is a scanning electron microscopy (SEM) micrograph of a conventional bone cement exhibiting agglomerates having 10-20 micrometer diameters.
Figure 6:
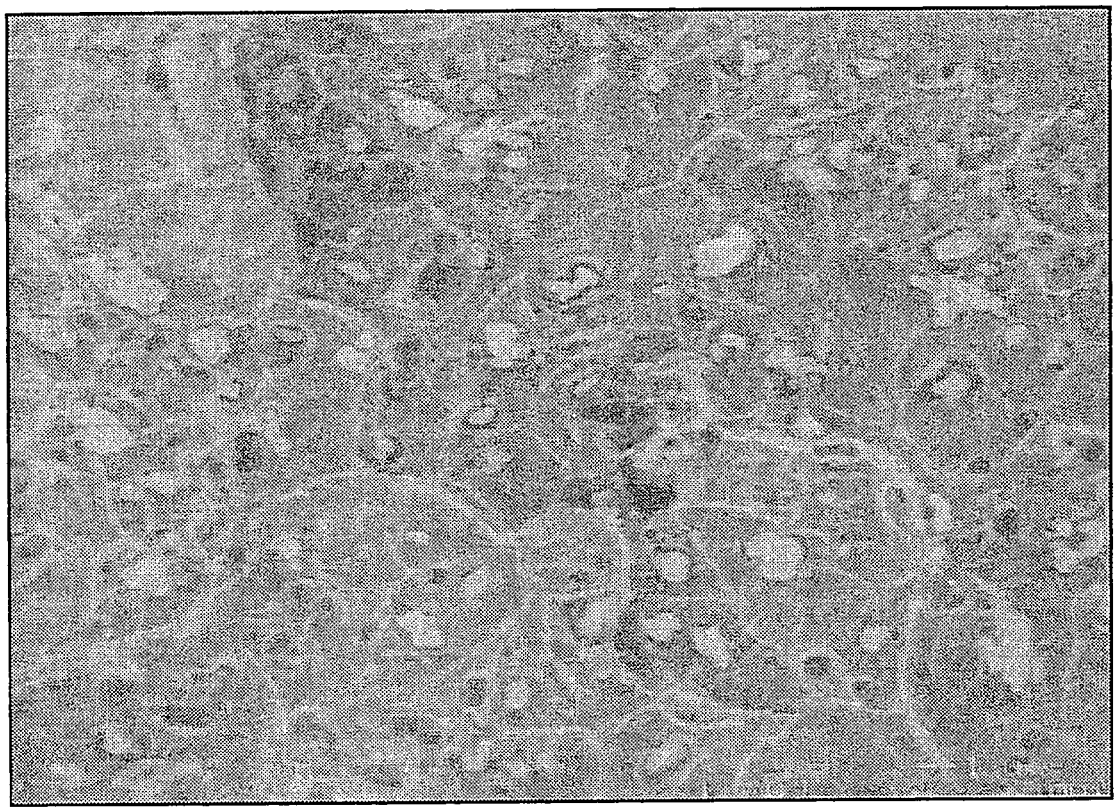
FIG. 6 is a scanning electron microspcopy (SEM) micrograph of a conventional bone cement including barium sulfate.
Figure 7:
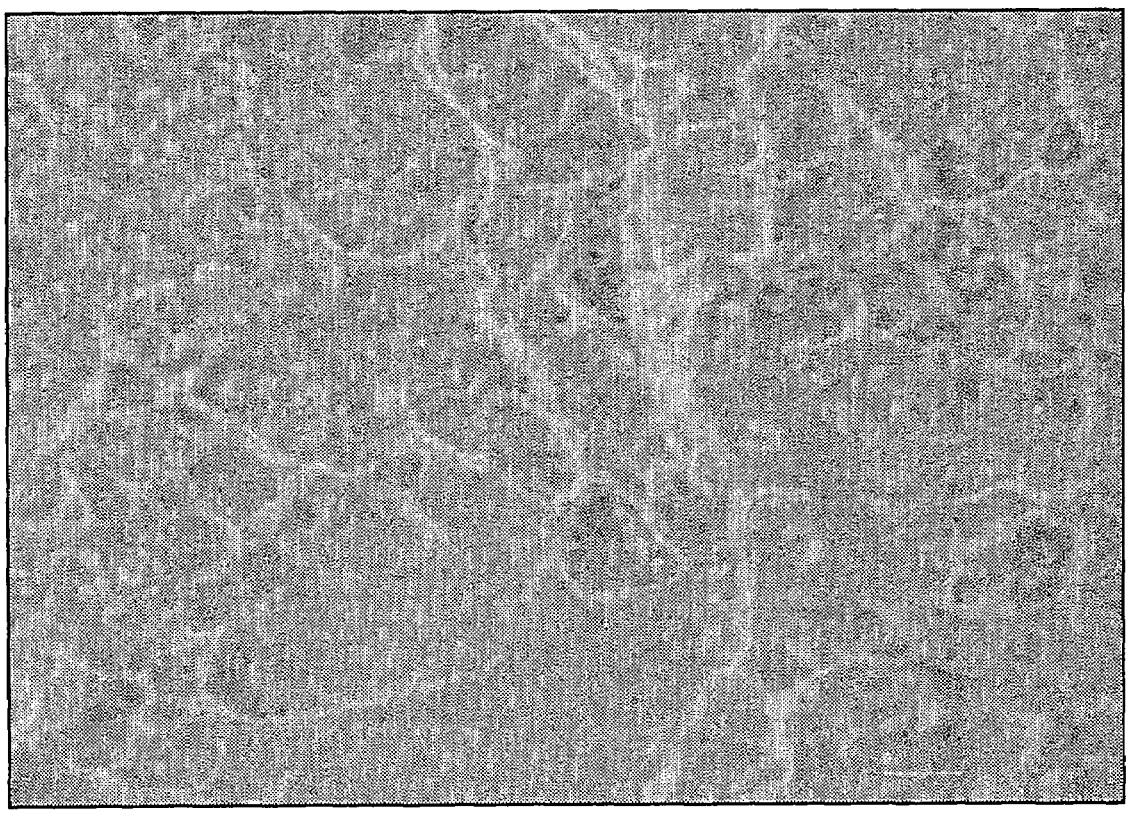
FIG. 7 is a scanning electron microscopy (SEM) micrograph of a cement which includes barium sulfate particles having a diameter of 100 nanometer.
Figure 8:
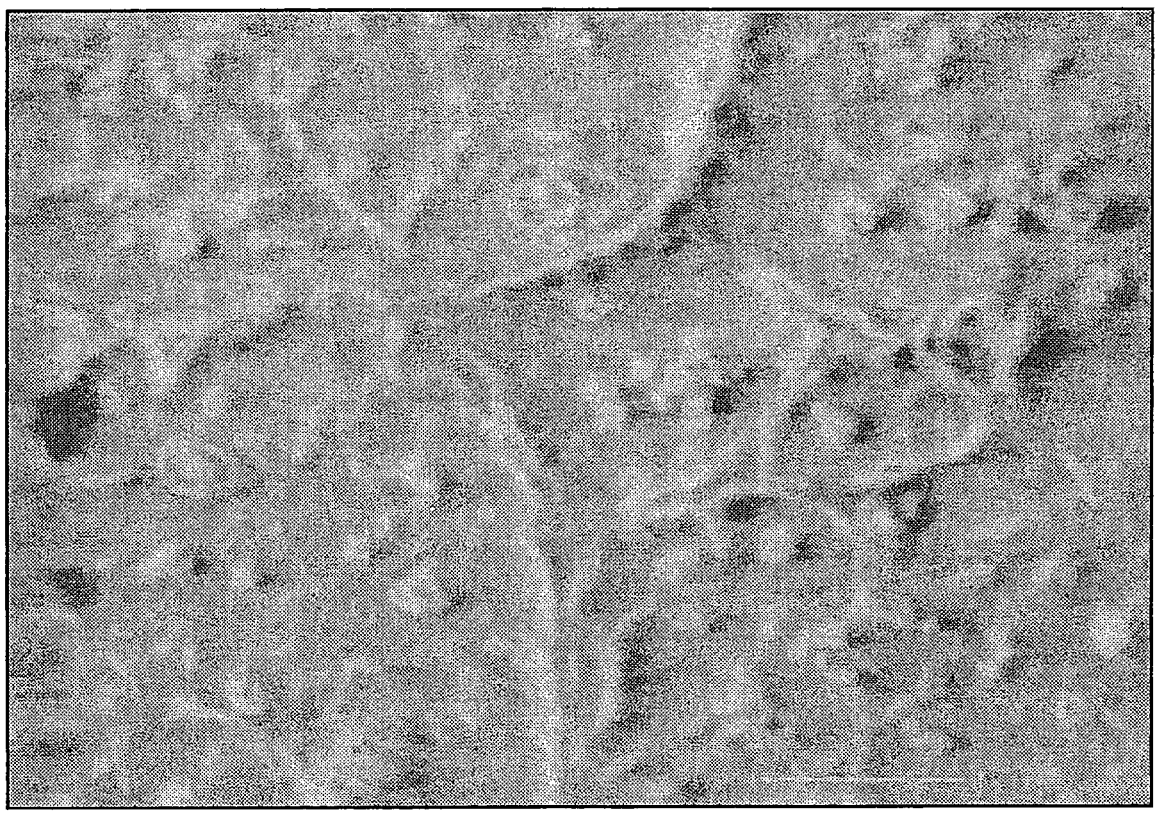
FIG. 8 is a scanning electron microscopy (SEM) micrograph of a cement which includes alumina particles having a diameter of 60 nanometer.

A JEOL 6320FV low voltage high resolution scanning electron microscope (SEM) was used to observe the particle morphology in all cements. This method was used to determine whether the particles agglomerated during the mixing and curing process, and to determine the matrix ligament thickness present in commercial cements as well as in the new cements fabricated in this invention. All cements were freeze fractured and their fracture surfaces were examined using the low voltage SEM operating at 1 kV. All cements were examined without applying any conducting coating to the fracture surfaces. SEM micrographs are present in FIGS. 4-8. FIG. 4 is a representative micrograph of radiolucent cement containing no barium sulfate. FIG. 5 shows 10-20 micrometer diameter agglomerates present in the cement. In general, the matrix ligament thickness of these cements is higher than 1 micrometer (see Table 3). However, due to agglomeration, the matrix ligament thickness increases since the average diameter of the particle agglomerates increases with increase in agglomeration, as per equation 1. FIG. 6 shows the dispersion of barium sulfate particles in SIMPLEX™ cements, while FIGS. 7 and 8 show the new cements containing 100 nanometer barium sulfate and 60 nanometer alumina particles, respectively. It can be observed that the matrix ligament thickness in the latter two cements is less than 300 nonometers while SIMPLEX™ has a matrix ligament thickness greater than one micrometer.

Image analysis (Scion Image 1.6) was used for calculation of the matrix ligament thickness of various bone cements. Of each image 5 regions of interest were used and 10 measurements taken of each region. The SEM scale bar was used for calibration. ANOVA analysis for repeated measurements was used. Table 3 shows the observed matrix ligament thickness for SIMPLEX™, the 100 nanometer barium sulfate containing cement and the 60 nanometer alumina containing cements.

TABLE 3

| Cement fillers | Mean Matrix Ligament Thickness (nanometer) | Standard Error of Mean (nanometer) |
|---|---|---|
| 1–3 μm Barium Sulfate | 1270 | 99 |
| 100 nm Barium Sulfate | 282 | 27 |
| 60 nm Aluminum Oxide | 232 | 23 |

In the latter two new cements, the matrix ligament thickness was substantially lower than 1 micrometer while SIMPLEX™ had a matrix ligament thickness greater than 1 micrometer.

These experiments showed that the surgical cements in which the matrix ligament thickness was lower than 1 micrometer had a higher work-of-fracture, regardless of whether the particles were barium sulfate or aluminum oxide.

While this invention has been particularly shown and described with references to preferred embodiments thereof, it will be understood by those skilled in the art that various changes in form and details may be made therein without departing from the scope of the invention encompassed by the appended claims.

What is claimed is:

1. A nanocomposite surgical material comprising:
   (a) a polymer matrix formed by polymerizing a liquid component and polymeric powder particles; and
   (b) nanoencapsulated solid filler dispersed within the polymer matrix to produce a composite surgical material having an average matrix ligament thickness of less than 1000 nanometers,
   wherein at least a portion of the filler has radio-opaque properties or includes at bioactive or pharmaceutical compound and is present in regions occupied by the polymerized liquid component.

2. The nanocomposite surgical material of claim 1 wherein the average matrix ligament thickness is less than 750 nanometers.

3. The nanocomposite surgical material of claim 1 wherein the average matrix ligament thickness is less than 500 nanometers.

4. The nanocomposite surgical material of claim 1 wherein the average matrix ligament thickness is less than 300 nanometers.

5. The nanocomposite surgical material of claim 1 wherein the polymer matrix is non-biodegradable.

6. The nanocomposite surgical material of claim 5 wherein the polymer matrix includes an acrylic polymer.

7. The nanocomposite surgical material of claim 1 wherein the polymer matrix of step (a) is formed by polymerizing the liquid component, wherein the liquid component comprises a monomer, and the polymeric powder particles, wherein the polymeric powder particles comprise a pre-polymerized polymer component.

8. The nanocomposite surgical material of claim 7 wherein the pre-polymerized polymer component is poly (methyl methacrylate), poly(methyl methacrylate-co-styrene) or any combination thereof, and the monomer is methyl methacrylate.

9. The nanocomposite surgical material of claim 1 wherein the nanocomposite surgical material is in the form of a pre-polymerized surgical implant.

10. The nanocomposite surgical material of claim 1 wherein the polymer matrix is biodegradable.

11. The nanocomposite surgical material of claim 10 wherein the polymer matrix includes polylactic acid.

12. The nanocomposite surgical material of claim 10 wherein the polymer matrix includes polyglycolic acid.

13. The nanocomposite surgical cement of claim 10 wherein the nanocomposite surgical material is in the form of a prepolymerized surgical implant.

14. The nanocomposite surgical material of claim 1 wherein the nanocomposite surgical material is a surgical cement.

15. The nanocomposite surgical material of claim 1 wherein the nanoencapsulated solid filler has an average mass diameter which is less than 1000 nanometers.

16. The nanocomposite surgical material of claim 1 wherein the nanoencapsulated solid filler has an average mass diameter ranging from about 750 nanometers to about 1 nanometer.

17. A nanocomposite surgical material comprising:
(a) a polymer matrix formed by polymerizing a liquid component and polymeric powder particles; and
(b) nanoencapsulated solid filler dispersed within the polymer matrix to produce a composite surgical material;
wherein the nanoencapsulated solid filler has an average mass diameter of less than 1000 nanometers and wherein at least a portion of the filler has radio-opaque properties or includes a bioactive or pharmaceutical compound and is present in regions occupied by the polymerized liquid component.

18. The nanocomposite surgical material of claim 17 wherein the nanoencapsulated solid filler has an average mass diameter ranging from about 750 nanometers and about 1 nanometer.

19. The nanocomposite surgical material of claim 1 wherein the solid filler is nanoencapsulated prior to addition of the polymeric powder.

20. The nanocomposite surgical material of claim 17 wherein the nanoencapsulated solid filler is nanoencapsulated prior to addition of the polymeric powder.

* * * * *